(12) United States Patent
Mayer et al.

(10) Patent No.: US 7,820,060 B2
(45) Date of Patent: Oct. 26, 2010

(54) SYNERGISTIC BIOCIDE AND PROCESS FOR CONTROLLING GROWTH OF MICROORGANISMS

(75) Inventors: Michael J. Mayer, Jacksonville, FL (US); Freddie L. Singleton, Switzerland, FL (US)

(73) Assignee: Hercules Incorporated, Wilmington, DE (US)

( * ) Notice: Subject to any disclaimer, the term of this patent is extended or adjusted under 35 U.S.C. 154(b) by 0 days.

(21) Appl. No.: 11/509,158

(22) Filed: Aug. 24, 2006

(65) Prior Publication Data

US 2007/0045199 A1   Mar. 1, 2007

Related U.S. Application Data

(60) Provisional application No. 60/711,508, filed on Aug. 26, 2005.

(51) Int. Cl.
*C02F 1/76* (2006.01)

(52) U.S. Cl. .................. 210/754; 162/161; 210/755; 210/756; 210/759; 210/760; 210/764; 422/37; 424/661; 424/664

(58) Field of Classification Search .................. 210/755
See application file for complete search history.

(56) References Cited

U.S. PATENT DOCUMENTS

| | | | | |
|---|---|---|---|---|
| 1,884,546 A * | 10/1932 | Bovard et al. | ............... | 162/161 |
| 1,989,380 A * | 1/1935 | Romans | ....................... | 210/755 |
| 2,678,258 A | 5/1954 | Haller | .......................... | 23/190 |
| 2,710,248 A | 6/1955 | Sisier et al. | ................... | 23/190 |
| 2,837,409 A | 6/1958 | Sisier et al. | ................... | 23/190 |
| 3,038,785 A | 6/1962 | Braude et al. | ................. | 23/190 |
| 3,488,164 A | 1/1970 | Grushkin et al. | .............. | 23/356 |
| 3,732,164 A * | 5/1973 | Pressley et al. | ............. | 210/752 |
| 4,239,622 A * | 12/1980 | Ridgway | ..................... | 424/616 |
| 5,070,200 A | 12/1991 | Raynor | ....................... | 544/242 |
| 5,976,386 A | 11/1999 | Barak | .......................... | 210/756 |
| 6,132,628 A | 10/2000 | Barak | .......................... | 210/756 |
| 6,149,835 A * | 11/2000 | Brown | ......................... | 252/175 |
| 6,315,950 B1 * | 11/2001 | Harp et al. | ..................... | 422/28 |
| 6,398,965 B1 * | 6/2002 | Arba et al. | ................... | 210/652 |
| 6,419,823 B2 * | 7/2002 | DeLonge et al. | ............. | 210/181 |

(Continued)

FOREIGN PATENT DOCUMENTS

| GB | 2 302 687 | 1/1997 |
|---|---|---|
| WO | WO/96/10541 | 4/1996 |
| WO | WO/2004/007378 | 1/2004 |

OTHER PUBLICATIONS

N. R. Ward, R. L. Wolfe & B. H. Olson: :"Effect of Ph, Application Technique and Chlorine-to Nitrogen Ratio on Disinfectant Activity of Inorganic Chloramines with Pure Culture Bacteria" Appl. Environ. Microbiol., vol. 48, No. 3, 1984.

Database WPI Week 199014, Derwent Publications Ltd., London, GB; AN 1990-102531 & JP 02052087 A (Toray Ind Inc.) Feb. 21, 1990.

F. W. Tilley & R. Chapin: "Germicidal Efficiency of Chlorine and the N-Chloro Derivatives of Ammonia, Methylamine and Glycine Against Anthrax Spores", J. Bacteriology, vol. 19, 1930.

*Primary Examiner*—Peter A Hruskoci
(74) *Attorney, Agent, or Firm*—Joanne Rossi (57) ABSTRACT

Synergistic mixtures of haloamines and their use to control the growth of microorganisms in aqueous systems are disclosed. The method of using the synergistic mixtures entails adding an effective amount of a monohaloamine and an effective amount of a dihaloamine to an aqueous system. The ratio of monohaloamine to dihaloamine is selected to result in a synergistic biocidal effect

19 Claims, 5 Drawing Sheets

(Note: pH 5 plate count for 0.5 mg/l DCA was calculated based on previous results due to sampling error)

U.S. PATENT DOCUMENTS

| | | | |
|---|---|---|---|
| 6,478,973 B1 | 11/2002 | Barak | 210/756 |
| 6,714,354 B2 * | 3/2004 | Trotter, Jr. | 359/652 |
| 6,773,607 B2 * | 8/2004 | Russell | 210/747 |
| 7,311,878 B2 * | 12/2007 | Singleton et al. | 422/37 |
| 7,387,736 B2 * | 6/2008 | Phillips et al. | 210/752 |
| 7,473,370 B2 * | 1/2009 | Kouame | 210/668 |
| 2005/0211643 A1 * | 9/2005 | Phillips et al. | 210/753 |
| 2006/0124558 A1 * | 6/2006 | Kouame | 210/764 |

* cited by examiner

SYNERGISTIC BIOCIDE AND PROCESS FOR CONTROLLING GROWTH OF MICROORGANISMS

This application claims the benefit of U.S. Provisional Application No. 60/711,508 filed Aug. 26, 2005, the entire contents of which are herein incorporated by reference.

TECHNICAL FIELD

The present invention relates to synergistic mixtures (or combinations) of haloamines and their use to control the growth of microorganisms in aqueous systems, more particularly in industrial process waters.

BACKGROUND OF THE INVENTION

Uncontrolled growth of microorganisms in industrial production systems can have serious consequences such as lowered product quality, degradation or spoilage of products, contamination of products, and interference with a wide range of important industrial processes. Growth of microorganisms on surfaces exposed to water (e.g., recirculation systems, heat exchangers, once-through heating and cooling systems, pulp and paper process systems, etc.) can be especially problematic, as many of these systems provide an environment suitable for growth of bacteria and other types of microorganisms. Industrial process waters often provide conditions of temperature, nutrients, pH, etc. that allow for abundant growth of microorganisms. Uncontrolled growth of microorganisms is often manifested in the water column with large numbers of free-floating (planktonic) cells as well as on submerged surfaces where conditions favor formation of biofilms.

The process leading to the formation of biofilms is described in detail as follows. The first stage of biofilm formation is for planktonic cells to contact submerged surfaces either as a result of turbulence in water flow or by active movement toward the surface. If the physical and chemical characteristics of surface, including the surface-water interface, are favorable for growth, microorganisms can attach to the surface, grow, and begin to produce exopolysaccharides that provide three-dimensional integrity to the biofilm. Over time, the biofilm becomes thicker and internally complex as cells reproduce and produce more exopolysaccharides. The microbial community of a biofilm can consist of single or multiple species.

Biofilms are seemingly ubiquitous in all natural, medical, and industrial settings where bacteria exist. Microorganisms can form biofilms on a wide variety of abiotic hydrophobic and hydrophilic surfaces, including glass, metals, and plastics.

Many types of processes, systems, and products can be adversely affected by uncontrolled growth of microorganisms in biofilms and in industrial process waters. Such problems include accelerated corrosion of metals, accelerated decomposition of wood and other biodegradable materials, restricted flow through pipes, plugging or fouling of valves and flow-meters, and reduced heat exchange or cooling efficiency on heat exchange surfaces. Biofilms may also be problematic relative to cleanliness and sanitation in medical equipment, breweries, wineries, dairies and other industrial food and beverage process water systems. Moreover, sulfate-reducing bacteria are often problematic in waters used for the secondary recovery of petroleum or for oil drilling in general. Although sulfate-reducing bacteria can form biofilms on equipment and in pipelines, the significant problem caused by these bacteria is that they generate metabolic by-products that have highly offensive odors, are toxic, and can cause corrosion of metal surfaces by accelerating galvanic action. For example, these microorganisms reduce sulfates present in the injection water to generate hydrogen sulfide, a highly toxic gas that has a highly offensive odor (i.e., rotten egg odor), is corrosive, and reacts with metal surfaces to form insoluble iron sulfide corrosion products.

Paper production is particularly susceptible to adverse effects of biofilms. Paper process waters have conditions (e.g., temperature and nutrients) that favor growth of microorganisms in the water and on exposed surfaces. Biofilms on surfaces in paper process systems can be very thick and contain paper fiber and other materials used in paper production; such resulting material is referred to as slime or a slime deposit. Slime deposits can become dislodged from system surfaces and become incorporated into the paper, which results in increased breaks and tears in the sheet. Furthermore, slime can cause unsightly blemishes or holes in the final product, which result in a lower quality product or the product being rejected. This necessitates stopping paper production to clean the equipment, which results in the loss of production time.

In order to control problems caused by microorganisms in industrial process waters, numerous antimicrobial agents (i.e., biocides) have been employed to eliminate, to inhibit or to reduce microbial growth. Biocides are used alone or in combination to prevent or control the problems caused by growth of microorganisms. Biocides are usually added directly to a process water stream or to a material used in the process. When used to prevent biofilm formation, the typical method of addition is such that the biocide is distributed throughout the process system. In this manner, planktonic microorganisms and those in biofilms on surfaces in contact with the process water can be controlled.

Many organic and inorganic substances are used as biocides in industrial process systems. The type of biocide used in a given system will depend on many factors including, but not limited to, the nature of the medium to which the biocide is added, the problematic microorganism(s), as well as specific requirements of the industry, including safety and regulatory considerations. Not all biocides are interchangeable. A biocide that works well on one environment may not work in another environment. For instance, biofilm forming organisms are difficult to control because many biocides can not penetrate the sheath formed around the organism.

Depending on their chemical composition and mode-of-action, biocides are classified as oxidizing or non-oxidizing. Oxidizing and non-oxidizing biocide can be used alone or in combination depending on the application. Oxidizing biocides have been widely used in industry for decades, especially in pulp and paper production where strong oxidizers have been used to control microbial populations. Oxidizing biocides such as chlorine gas, sodium hypochlorite, hypobromous acid, and chlorine dioxide are widely used as biocides to treat recirculating waters in many types of industries. Two of the primary reasons for using these and other oxidizing biocides is that such oxidizers are: (1) inexpensive; and (2) non-specific regarding which types of microorganisms are inhibited; if sufficient concentrations of oxidizing biocides are achieved virtually all microorganisms can be inhibited.

Of the oxidizing biocides, chlorine is the most widely used to treat recirculating water systems. The chemistry of chlorine is well known. Other halogens such as Bromine, Fluorine, and Iodine are known to have antimicrobial activity. When added to water, chloride can exist in either of two forms, HOCl and OCl$^-$, depending on pH. Bromine reacts with water similar to chlorine. These chemical species of chlorine, also referred to as "free chlorine," react with a wide variety of compounds in aqueous systems.

HOCl (hypochlorous acid) is much more effective as a disinfectant than OCl⁻ (hypochlorite). When HOCl contacts a microorganism, the oxidizer can rapidly interact with any of a number of cellular constituents resulting in inhibition of growth. It has been reported that a very short contact time (i.e., <0.1 sec) is required to inhibit a cell. Chlorine contacting a microorganism may rapidly cause a Fenton-type reaction in which hydroxyl radicals are generated and those radicals are responsible inhibitory effects.

The highly reactive nature of chlorine may also be a liability, as some of the oxidizer will be used (e.g., consumed) during reactions with non-biological material. Therefore, in order to provide enough oxidizer to react with microorganisms in a process stream, the total amount of oxidizer needed to inhibit microorganisms will include that used in reactions with non-biological components of the system. Reactions with non-biological components of process water not only add to treatment cost, but undesired by-products can be generated and other additives in the process stream can be adversely affected.

Process streams such as in paper mills are especially problematic for highly reactive oxidizers because of the high concentrations of dissolved and particulate inorganic and organic materials. Such process waters exhibit a very high "demand" on the oxidizer. "Demand" is defined as the amount of chlorine that reacts with substances other than the target microorganisms in the process water. In order to maintain an effective concentration of chlorine in an aqueous system to inhibit microorganisms, an amount in excess of the demand must be applied. The types and amounts of inorganic and organic materials in a process stream will define the demand for an oxidizer. For example, many substances are known to react with chlorine and result in the chlorine being non-biocidal; such substances include sulfides, cyanides, metal ions, lignin, and, among others, various water treatment chemicals (e.g., some scale and corrosion inhibitors).

Although effective as biocides, strong oxidizers such as sodium hypochlorite can cause many problems in an industrial process stream such as increased corrosion rates, increased consumption of wet end additives, and, among others, decreased life of felts used on paper machines.

Because of the inherent reactivity of chlorine and related strong oxidizers with non-biological organic and inorganic materials, it is desirable to have the oxidizer in a form that would have antimicrobial activity but be less reactive with non-biological materials. The process of chloramination has been used to avoid some of the problems associated with the use of strong oxidizers. Chloramination can occur in a number of ways (1) adding chlorine to a water system that contains a known, low concentration of ammonia, or (2) adding ammonia to a water system that contains a known, low concentration of chlorine. In either situation, the chlorine and ammonia react in situ to form a chloramine. Chloramines generated from reacting chlorine and ammonia include monochloramine ($NH_2Cl$), dichloramine ($NHCl_2$), and trichloramine ($NCl_3$). Two of the important parameters that determine which chloramine species will exist in a system are pH and the ratio of Cl to N.

Chlorine, as a gas or liquid, and ammonia are commonly combined to form chloramines. Other halogens such as bromine can be substituted for chlorine. Other substances containing an amine ($RNH_2$) group can also form haloamines, such as chloramines. The antimicrobial activity of a chloramine depends on the chemical nature of the amine-containing compound. For example, ammonium hydroxide can react with an oxidizing halogen donor such as sodium hypochlorite to form monochloramine; this chloramine will be an effective biocide. However, if an amino acid, such as glycine ($NH_2CH_2COOH$) is reacted with sodium hypochlorite, the amine group will be chlorinated, forming a mono- or di-chloramine species. The chlorinated glycine has less antimicrobial activity compared to monochloramine generated from ammonium hydroxide.

Chloramines are attractive for water treatment because of their stability in situ, ease of application and monitoring, and low capital and operational costs. Although laboratory studies have demonstrated that free chlorine is more effective than chloramines at inactivating microorganisms, studies have also documented that the antimicrobial activity of chloramines is greater at lower pH as well as higher temperatures and concentrations.

Methods for production of chloramines in highly concentrated form, including anhydrous chloramine, have been patented (U.S. Pat. Nos. 2,678,258; 2,837,409; 3,038,785; 2,710,248; and 3,488,164, the contents of each is herein incorporated by reference).

Monochloramine is the preferred chemical species for disinfecting a water supply. Dichloramine is reported to be a superior disinfectant but has negative properties such has high volatility and odor. The difference in reactivity and specificity of chlorine and monochloramine may allow the latter to penetrate a biofilm and react with the denizens whereas the former is consumed in non-specific reactions with materials in the water or abiotic components of the biofilm before it fully penetrates the biofilm.

Monochloramine is used as a single active to treat water for controlling growth of microorganisms in water and wastewater systems. Studies have shown that the pH of an aqueous system affects efficacy of monochloramine; the efficacy increases as pH decreases. Other physical and chemical parameters of a system can affect efficacy of chloramines by influencing the stability of the compounds. For example, it has been demonstrated that parameters such as pH, temperature, and the presence of other chemicals have influence on the stability of monochloramine in water, monochloramine has a significantly longer stability at 4° C. than it does at 35° C.

Although widely practiced for treating municipal water distribution systems, chloramines are not commonly used in industrial systems. Chlorine (in bleach or chlorine gas) was used in combination with ammonia in papermaking systems. There was a shift toward using other oxidizing and non-oxidizing biocides in papermaking systems in subsequent years. However, recently there appears to be renewed interest in using chloramines in papermaking systems (see U.S. Pat. Nos. 6,478,973; 6,132,628; 5,976,386, the contents of each is herein incorporated by reference). For example, it has been shown that ammonium bromide activated with sodium hypochlorite produces an effective biocide for industrial applications. Furthermore, this biocide is especially effective for controlling problems associated with microbial growth in pulp and paper process waters that have a pH in the alkaline range. The biocide generated from ammonium bromide, described as a "bromide-activated chloramine," effectively reduces the total microbial community within a system (i.e., biofilm-associated as well as planktonic bacteria) where the pH is neutral to alkaline. The preferred pH of the receiving water should be in the range of 7 to 9; the biocide is effective in alkaline paper process water but does not interfere with other pulp and paper process and functional additives (e.g., wet and dry strength additives, size agents, dyes, etc), unlike other common oxidizer programs.

There remains a need for improved biocides that are effective under harsh environmental conditions such as found in the papermaking industry and other industrial processes.

SUMMARY OF THE INVENTION

The present invention relates to the use of certain mixtures (or combinations) of haloamines and processes or methods to prevent the growth of microorganisms in industrial process waters.

More specifically the present invention is directed to the use of synergistic mixtures (or combinations) containing monohaloamine and dihaloamine, examples of such are monochloramine and dichloramine. In the invention microbial populations in aqueous industrial process waters are controlled by administering effective amounts of monohaloamine and dihaloamine to aqueous systems, the result is synergistic.

The novel mixtures (or combinations) of haloamines and processes (methods) incorporating the composition of the present invention show unexpected synergistic activity against microorganisms.

DETAILED DESCRIPTION OF THE INVENTION

For the purposes of this invention, haloamines are defined as chemicals with a composition that includes one or more halogen atoms associated with an amine group and possess antimicrobial activity. The nitrogen may or may not be bonded to another atom other than hydrogen. Halogen atoms include chlorine, fluorine, bromine, and iodine. Chlorine is the most preferred halogen used in the present invention.

The present invention is directed to novel synergistic biocidal mixtures (or combinations) comprising monohaloamine and dihaloamine such as monochloramine and dichloramine, in an aqueous system. These novel synergistic biocidal mixtures (or combinations) when used in combination in an aqueous system are effective in inhibiting or controlling the growth of microorganisms in the aqueous system. The present invention is also directed to a method of inhibiting or controlling the growth of microorganisms by administering or adding an effective amount of monohaloamine and an effective amount of dihaloamine, to result in a synergy index of less than 1 as defined herein. The preferred haloamines are chloramines and bromamine.

Monohaloamine, when used with dihaloamine in aqueous systems, unexpectedly provided enhanced biocidal activity, which is greater than that of the individual components. The microbiocidal mixtures (or combinations) of the present invention possess a high degree of antimicrobial activity which could not have been predicted from the known activities of the individual ingredients comprising the combinations. The enhanced activity of the mixtures (or combinations) permits a significant reduction in the total quantity of the biocide required for an effective treatment of an aqueous system.

The aqueous systems to be treated have pH values of between 4 and 10, preferable between 5 and 9.

Monohaloamine, when used with dihaloamine in aqueous systems, unexpectedly provided enhanced biocidal activity, which is greater than that of the individual components. Examples of monohaloamines and dihaloamines include chloramines, bromamines, and iodoamines. The microbiocidal mixtures (or combinations) of the present invention possess a high degree of antimicrobial activity which could not have been predicted from the known activities of the individual ingredients comprising the combinations. The enhanced activity of the mixtures (or combinations) permit a significant reduction in the total quantity of the biocide required for an effective treatment of an aqueous system.

Because of the inherent reactivity of halogens, for example chlorine, and related strong oxidizers with non-biological organic and inorganic materials, it is desirable to have the oxidizer in a form that would have antimicrobial activity but be less reactive with non-biological materials. The process of chloramination has been used to avoid some of the problems associated with the use of strong oxidizers. The process of chloramination can generate chloramines including monochloramine ($NH_2Cl$), dichloramine ($NHCl_2$), and trichloramine ($NCl_3$). Two of the important parameters that determine which chloramine species will exist in a system are pH and the ratio of Cl to N. As the pH of the aqueous system is decreased the monohaloamine species will convert to a dihaloamine species. As the amount of chlorine in the system increases with respect to the amount of available amine source the equilibrium pushes the monohaloamine species to a dihaloamine species.

Chlorine, as a gas or liquid, and ammonia are commonly combined to form chloramines. However, other substances containing an amine group can also form chloramines or haloamines. The antimicrobial activity of a haloamine such as chloramine depends on the chemical nature of the amine-containing compound. For example, ammonium hydroxide can react with an oxidizing halogen donor such as sodium hypochlorite to form monochloramine; this chloramine will be an effective biocide. However, if an amino acid, such as glycine ($NH_2CH_2COOH$) is reacted with sodium hypochlorite, the amine group will be chlorinated, forming a mono- or di-chloramine species. The chlorinated glycine has less antimicrobial activity compared to monochloramine generated from ammonium hydroxide.

The present invention is relates to synergistic mixtures (or combination) containing monohaloamine and dihaloamine. Haloamines, both monohaloamine and dihaloamine, can be produced by combining an amine source or ammonium source with a halogenated oxidant. An amine source or ammonium source can be combined with a non halogenated oxidant to form a haloamine if the system also contains a halogen source. Examples of halogen sources include but are not limited to, a halogen containing salt or acid. Examples of haloamines are chloramines (monochloramine or dichloramine) and bromamines (monobromamine and dibromamine). The haloamine mixture can be adjusted to obtain the desired ratio of monohaloamine to dihaloamine by adjusting the pH and/or the halogen to nitrogen ratio. Once monochloramine is converted to dichloramine it is stable and does not readily convert back.

Dichloramine can be produced from a monochloramine solution. One method of producing dichloramine from monochloramine is to reduce the pH of the monochloramine solution. Another method of producing a dichloramine from a monochloramine solution is to adjust the chlorine to nitrogen ratio in the solution, for example by adding additional chlorine to the monochloramine solution. Once monochloramine is converted to dichloramine it is stable and does not readily convert back. The pH and the Cl to N ratios can be balanced to produce the desired blend of mono and dichloramines. Monobromamine readily converts to dibromamine at pH's below 12. Under most conditions, at pH of 10 or less, bromamine will exist as dibromamine.

Any method that can be used to produce a haloamine is contemplated as a possible source of haloamine for the purposes of this invention. The ratio of monohaloamine to dihaloamine can be adjusted by known methods to achieve the desire ratio that produces a synergistic biocidal effect.

In one variation of the invention, an amine or ammonium source is reacted with a halogen containing oxidant to produce monohaloamine. The pH of the monohaloamine is then adjusted to achieve the desired ratio of mono to di haloamines.

In another variation, an amine or ammonium source is reacted with a halogen containing oxidant to produce monohaloamine. The chlorine to nitrogen ratio of the monohaloamine is then adjusted to achieve the desired ratio of mono to di haloamines.

In a third variation, an amine or ammonium source is reacted with a halogen containing oxidant to produce monohaloamine. A portion of the monohaloamine is then separated and adjusted to produce dihaloamine. The dihaloamine and the monohaloamine are used in a ratio in the system to be treated to achieve the desired ratio of mono to di haloamines.

In a fourth variation, the monohaloamine and the dihaloamine are produced separately and contacted with the aqueous system to be treated separately or in a common conduit. The amounts of mono and di chloramines are selected to achieve the desired ratio of mono to di haloamines to produce the synergistic effect.

The amine sources or ammonium sources used in the present invention include, but are not limited to, ammonia and ammonium salts and amines. What is meant by ammonium salts are those salts that have a $NH_4^+$ cation and a related anion. Examples of ammonium salts include, but are not limited to, ammonium acetate, ammonium bicarbonate, ammonium bifluoride, ammonium bromide, ammonium carbonate, ammonium chloride, ammonium citrate, ammonium fluoride, ammonium hydroxide, ammonium iodide, ammonium molybdate ammonium nitrate, ammonium oxalate, ammonium persulfate, ammonium phosphate, ammonium sulfate, ammonium sulfide, ferric ammonium sulfate, ferrous ammonium sulfate and ammonium sulfamate. Preferred ammonium salts are ammonium carbonate, ammonium citrate, ammonium hydroxide, ammonium sulfate and ammonium chloride. Quaternary ammonium salts are not considered amine sources for the present invention and are not included in the term ammonium salts for the purposes of this invention.

The amine sources useful in the present invention can also be primary amines ($RNH_2$), secondary amines ($R_2NH$) or tertiary amines ($R_3N$). Additional ammonium and/or amine sources included ammonia, dimethylamine, ethanolamine, ethylenediamine, diethanolamine, triethanolamine, dodecylethanolamine, hexdecylethanolamine, oleic acid ethanolamine, triethylenetetramine, dibutylamine, tributylamine, glutamine, dilaurylamine, distearylamine, tallow-methylamine, coco-methylamine, n-alkylamines, n-acetylglucosamine, diphenylamine, ethanolmethylamine, diisopropanolamine, n-methylaniline, n-hexyl-n-methylamine, n-heptyl-n-methylamine, n-octyl-n-methylamine, n-nonyl-n-methylamine, n-decyl-n-methylamine, n-dodecyl-n-methylamine, n-tridecyl-n-methylamine, n-tetra-decyl-n-methylamine, n-benzyl-n-methylamine, n-phenylethyl-n-methylamine, n-phenylpropyl-n-methylamine, n-alkyl-n-ethylamines, n-alkyl-n-hydroxyethylamines, n-alkyl-n-propylamines, n-propylheptyl-n-methylamine, n-ethylhexyl-n-methylamine, n-ethylhexyl-n-butylamine, n-phenylethyl-n-methylamine, n-alkyl-n-hydroxypropylamines, n-alkyl-n-isopropylamines, n-alkyl-n-butylamines and n-alkyl-n-isobutylamines, n-alkyl-n-hydroxyalkylamines, hydrazine, urea, guanidines, biguanidines, polyamines, primary amines, secondary amines, cyclic amines, bicyclic amines, oligocyclic amines, aliphatic amines, aromatic amines, primary and secondary nitrogen containing polymers. Quaternary amines are not included in the amine source useful in this invention. Quaternary amines are saturated and unreactive with the oxidants. They do not react sufficiently to produce the biocide of the present invention Oxidants are reacted with the amine source to produce the biocides useful in the present invention. The oxidants used in the present invention include, but are not limited to, chlorine, hypochlorite, hypochlorous acid, chlorine dioxide, chlorinated isocyanurates, bromine, hypobromite, hypobromous acid, bromine chloride, electrolytically-generated chlorites, electrolytically-generated bromites, halogenated hydantoins, ozone, and peroxy compounds such as perborate, percarbonate persulfate, hydrogen peroxide, percarboxylic acid, and peracetic acid.

In one particular advantageous embodiment of the invention, the ammonium and/or amine source is ammonium hydroxide and the oxidant is sodium hypochlorite.

In another particular advantageous embodiment of the invention, the ammonium and/or amine source is ammonium sulfate and the oxidant is sodium hypochlorite.

The biocidal mixtures or methods of this invention are effective for controlling and inhibiting the growth and reproduction of microorganisms in aqueous systems and additive aqueous systems. Aqueous systems include industrial waters systems such as cooling water systems, pulp and paper systems, petroleum operations, industrial lubricants and coolants, lagoons, lakes and ponds. Aqueous systems include additive aqueous systems. In addition, the aqueous systems in which the present invention can be used include, but are not limited to, those involved in, paints, leather, wood, wood pulp, wood chips, starch, clays, retention aids, sizing agents, defoamers, dry and wet strength additives, pigment slurries (e.g., precipitated calcium carbonate), proteinaceous materials, lumber, animal hides, vegetable tanning liquors, cosmetics, toiletry formulations, emulsions, adhesives, coatings, metalworking fluids, swimming pool water, textiles, heat exchangers, pharmaceutical formulations, geological drilling lubricants, and agrochemical compositions.

An additive aqueous system is an aqueous system that is or will be added into a larger aqueous system. Such aqueous additive systems in the pulp and paper industry include, but are not limited to, retention aids, sizing agents, defoamers, dry and wet strength additives and pigment slurries.

The dosage amounts of the monohaloamine and dihaloamine required for effectiveness in this invention generally depend on the nature of the aqueous system being treated, the level of organisms present in the aqueous system, and the level of inhibition desired. A person skilled in the art, using the information disclosed herein could determine the amount necessary without undue experimentation.

Effective concentrations of monohaloamine, such as monochloramine, on an active level basis, are from about 0.01 milligram per liter (mg/l) to about 1000 mg/l by weight, (i.e., based on the weight of monohaloamine as measured by the amount of available chlorine [in mg/l]) and preferably from about 0.05 to about 200 mg/l, more preferably from about 0.1 mg/l to about 100 mg/l, more preferably from about 0.1 mg/l to about 10 mg/l and even more preferably from about 0.1 mg/l to about 5 mg/l. The amount of dihaloamine, on an active level basis, is from about 0.01 parts per million (mg/l) to about 1000 mg/l by weight (i.e., based on the weight of dihaloamine as measured by the amount of available chlorine [in mg/l]), and preferably from about 0.05 to about 200 mg/l, more preferably from about 0.1 mg/l to about 100 mg/l, more preferably from about 0.1 mg/l to about 10 mg/l and even more preferably from about 0.1 mg/l to about 5 mg/l. Thus, with respect to the biocides, the lower and upper limits of the required concentrations substantially depend upon the system to be treated.

The ratio of monohaloamine to dihaloamine is from about 400:1 to about 1:100, preferably about 200:1 to about 1:100, preferably from about 20:1 to about 1:5.

In one embodiment of the invention monohaloamine is added to the aqueous system before dihaloamine. In another embodiment of the invention dihaloamine is added before the monohaloamine. In yet another embodiment of the invention, monohaloamine and dihaloamine are added simultaneously to the system to be treated.

In another embodiment, after the addition of monohaloamine, dihaloamine is added to the aqueous system. The time lag between the addition of monohaloamine and dihaloamine can be, but is not limited to, up to 30 minutes, or up to 15 minutes, or up to 5 minutes, or up to 1 minute.

In another embodiment, after the addition of dihaloamine, monohaloamine is added to the aqueous system. The time lag between the addition of dihaloamine and monohaloamine can be, but is not limited to, up to 30 minutes, or up to 15 minutes, or up to 5 minutes, or up to 1 minute.

In yet another embodiment, monohaloamine and dihaloamine are added to the aqueous system simultaneously.

In yet another embodiment the mixed haloamine blend can be produced in situ by addition of ammonium or amine source and halogenated oxidizer to the process water to cause formation of the monochloramine after which a measurable amount of acid is added to the water to lower the pH to a point sufficient to cause formation of dichloramine.

In any embodiment, monohaloamine can be added pursuant to any known method that provides the desired concentration of monohaloamine in the aqueous system. Similar to monohaloamine, in any embodiment, dihaloamine can be added pursuant to any known method that provides the desired concentration of dihaloamine in the aqueous system. Either or both monohaloamine and dihaloamine can be feed continuously, intermittently, or alternately to aqueous systems.

The haloamines can be added to the system as independent material(s) or in combination with other materials being added to the aqueous system being treated system. For example, a synergistic combination of monohaloamine and dihaloamine can be added with starch, clay, pigment slurries, precipitated calcium carbonate, retention aids, sizing aids, dry and/or wet strength additives, defoamers or other additives used in the manufacturing of pulp or paper products.

The haloamines can be continuously, intermittently, or alternately added to aqueous and/or additive systems. The above feed strategies for biocide addition are dependent on the growth of the microbial population, the type of problematic microorganisms and the degree of surface fouling in a particular system. A monohaloamine and dihaloamine blend can be used in the treatment of additive systems, (i.e., starch makedown solutions, retention aid makedown solutions, precipitated calcium carbonate slurries, etc.) or other feed points within the aqueous system (i.e., short or long loop, broke chest, saveall, thick stock, blend chest, head box).

EXAMPLES

The efficacies of the active materials and blends were determined using a dose protocol. The actives were evaluated in synthetic white water (see Smith et al., U.S. Pat. No. 6,361,963) with pH values of 5.5 and 8.0. The materials were tested against multi-species bacterial consortium (also referred to as an artificial consortium) containing approximately equal numbers of six bacterial strains. Although the test strains are representative of organisms present in paper mill systems, the effect is not limited to these bacteria. Two of the strains were *Klebsiella pneumonia* (ATCC 13883) and *Pseudomonas aeruginosa* (ATCC 15442). The other four strains were isolated from paper mill systems and have been identified as *Curtobacterium flaccumfaciens, Burkholderia cepacia, Bacillus maroccanus*, and *Pseudomonas glathei*. Each strain was grown on Tryptic Soy Agar overnight at 37° C. Sterile cotton-tipped swabs were used to aseptically transfer cells to a sterile solution of saline. Each cell suspension was prepared to a desired concentration as measured by turbidity before equal volumes of each strain were then combined to prepare the consortium. The bacterial consortium was distributed into the wells of a microtiter plate before additions of monohaloamine and/or dihaloamine were made. The microtiter plates were incubated at 37° C. Optical density (O.D.) readings at 650 nm were taken initially ($t_0$) and after time 4 hours ($t_4$) of incubation.

The raw data are converted to "bacterial growth inhibition percentages" according to the following formula:

% Inhibition=$[(a-b)\div a]*100$ where:
a=(O.D. of control at $t_n$)−(O.D. of control at $t_0$)
b=(O.D. of treated at $t_n$)−(O.D. of treated at $t_0$)

The inhibition values can be plotted versus dosage for each active and the particular blend. This results in a dose response curve from which the dosage to yield 50% inhibition ($I_{50}$) can be calculated. In the examples (tables) below, the $I_{50}$ values are expressed as mg/l of active material.

The synergism index (SI) was calculated by the equation below and is based on the amount needed to result in a 50% inhibition of bacterial growth.

Synergy Index (*SI*)=$(QA\div Qa)+(QB\div Qb)$ where:
QA=quantity of compound A in mixture, producing the end point
Qa=quantity of compound A, acting alone, producing the end point
QB=quantity of compound B in mixture, producing the end point
Qb=quantity of compound B, acting alone, producing the end point If SI is less than 1, synergism exists; if SI is greater than 1, antagonism exists; if SI is equal to 1, an additive effect exists.

The antibacterial efficacy of monochloramine and dichloramine alone and in combination were compared in a standard challenge assay. To perform the assay, artificial bacterial consortia were prepared using the same species as those in the microtiter assays. A mineral salt solution was prepared by combining $K_2HPO_4$ (1.2 mg/l), $KH_2PO_4$ (0.624 mg/l), $(NH_4)_2SO_4$ (0.05 g/l), and NaCl (0.1 mg/l). This solution was sterilized by autoclaving (121° C., 15 min) and, after cooling, it was amended with the following: 10 ml/l of filter sterilized solution of 0.5% (w/v) of $CaCl_2.6H_2O$; 10 ml/l of filter sterilized solution of 2% $MgSO_4.7H_2O$; filter-sterilized glucose (0.01 g/l, final concentration); 1 ml of a filter-sterilized solution containing $Na_2EDTA$ (ethylene diamine tetra acetate) (1.58 g/100 ml), $ZnSO_4.7H_2O$ (0.7 g/100 ml); $MnSO_4\_H_2O$ (0.18 g/100 ml); $FeSO_4.7H_2O$ (0.16 g/100 ml); $COCl_2.6H_2O$ (0.052 g/100 ml); $NaMoO_4.2H_2O$ (0.042 g/100 ml); and $CuSO_4.5H_2O$ (0.047 g/100 ml). Equal volumes of cell suspensions of each strain were then combined to prepare the consortium. The bacterial consortium was distributed into sterile glass containers and immediately used in challenge studies. To determine the effect of pH of the mineral salt solution on efficacy of monochloramine, dichloramine, and combinations thereof, the pH of the cell suspension was adjusted to desired levels using dilute solutions of sodium hydroxide or phosphoric acid, as appropriate. The pH values tested in the challenge studies were 5.0, 6.0, 7.0, and 8.0. The pH values represent the pH of whitewater typical of the majority of paper mills.

The presence of the active chemical species was demonstrated with a scanning spectrophotometer by measuring absorbance of light in the range of 200 nm to 350 nm. To determine the absorbance spectrum, a quantity of monochloramine and/or dichloramine in solution was added to a quartz cuvette and scanned in the spectrophotometer. The resulting spectral profile of the solution demonstrated the presence of either or both active chemical species and is consistent with published spectra of monochloramine and dichloramine.

The height of the absorbance peak at 244 nm was linearly related to concentration of monochloramine in the solution. Likewise, the absorbance peak at 295 nm was linearly related to the concentration of dichloramine in solution. Monitoring the peak height allowed the concentrations of monochloramine and dichloramine to be verified in the assay solutions. The UV absorption $NHBr_2$ is known to be at 350 nm, $NH_2Br$ is at 278 nm, OCl– is at 292 nm and OBr– is at 329 nm.

After the monohaloamine solution was prepared, the quantity needed to achieve a desired final concentration was transferred to the previously prepared bacterial consortium. Samples of the bacterial consortium were collected immediately before addition of the monochloramine and after contact times, usually 1, 10, and 20 minutes. Controls were untreated cell suspensions.

Use of the term "percentage" in reference to concentration of chemicals is based on a weight per volume basis.

Concentrations of monochloramine and dichloramine reported herein are in units of milligrams per liter as $Cl_2$. The units, milligrams per liter as $Cl_2$ (or mg/ml as $Cl_2$ or mg/ml), were determined on the basis of the total available chlorine concentration in a sample according to the Hach DPD chlorine test (Hach Company, Loveland, Colo.). Total available chlorine refers to the amount of chlorine in a sample that reacts with N,N-diethyl-p-phenylenediamine oxalate, the indicator used in the Hach assay. To determine the amount of monochloramine or dichloramine in a sample, an aliquot of the samples was transferred to a clean container, diluted with deionized water, as appropriate, and assayed according to the Hach DPD chlorine test. The assay measures the total amount of chlorine that can react with the indicator reagent. The reaction is measured by determining the absorbance of light at 530 nm. Therefore, for the purposes of this invention, a quantity of monochloramine or dichloramine presented in units of mg/l signifies that amount of monochloramine or dichloramine that contains the designated amount of milligrams per liter of reactive chlorine. Thus, for example, a sample treated with 1 mg/l monochloramine or dichloramine will contain a total available chlorine concentration of 1 mg/l. Similarly, a sample treated with 0.5 mg/l monochloramine and 0.5-mg/l dichloramine will contain a total available chlorine concentration of 1 mg/l.

Use of the term "ratio" in regard to the active molecules tested is based on the amount of each active on a milligram per liter basis. For example, a solution containing a 1:1 ratio of monochloramine to dichloramine would contain X mg/l (as $Cl_2$) of monochloramine and X mg/l as $Cl_2$) dichloramine, where X=a fraction or whole number. Likewise, a solution containing a 5:1 ratio of monochloramine to dichloramine would contain 5X mg/l (as $Cl_2$) of monochloramine and X mg/l as $Cl_2$) dichloramine, where X=a fraction or whole number.

Monochloramine can be generated using amine sources such as ammonium bromide, ammonium sulfate, ammonium hydroxide, ammonium phosphate, ammonium chloride etc. Ammonium hydroxide was used as the amine source to generate the haloamine in the present examples.

To perform a challenge study, monochloramine was prepared to a desired concentration by mixing appropriate quantities of 30% ammonium hydroxide and 6.2% percent sodium hypochlorite in a volume of deionized water in such a manner as to achieve equimolar ratios of $Cl^-$ and $NH_2^+$. After preparation of the monochloramine solution, the purity of the solution was verified by determining its absorbance spectrum. To prepare a dichloramine solution, the pH of a monochloramine solution was adjusted to down to 5.0. This ensured conversion of monochloramine to dichloramine. The spectral characteristics of the dichloramine solutions demonstrated that decreasing the pH of a monochloramine solution in deionized water did result in the formation of dichloramine. The concentrations of monochloramine and dichloramine in the solutions were confirmed by measuring total chlorine concentration by Hach DPD chlorine test.

Spectral analysis was used to verify the conversion of monochloramine to dichloramine when the pH was adjusted.

The following examples are intended to be illustrative of the present invention. However, these examples are not intended to limit the scope of the invention or its protection in any way. The examples illustrate the synergistic relationship obtained with the compositions of the present invention.

Example 1

A measured amount of monochloramine and a measured amount of dichloramine were added to a suspension of bacteria and the cell suspension incubated for a selected time period. The effectiveness of the combination of biocides was determined by measuring growth or lack thereof after an additional appropriate incubation time. This example illustrates the synergistic activity between monochloramine and dichloramine under a concurrent feed strategy against an artificial bacterial consortium in synthetic white water at pH 5.5 and 8.0. A synergy index value of <1.00 indicates a synergistic effect between the two actives.

TABLE 1

Synergy indices of combinations of monochloramine and dichloramine.

| mg/l NHCl$_2$ | mg/l NH2Cl | Ratio NHCl$_2$:NH$_2$Cl | % Inhibition | Synergy Index |
|---|---|---|---|---|
| NH$_2$Cl & NHCl$_2$ @ pH 5.5 | | | | |
| 17.23 | 0.00 | — | 50 | 1.00 |
| 15.13 | 0.73 | 20.8:1.0 | 50 | 0.92* |
| 14.03 | 1.45 | 9.7:1.0 | 50 | 0.89* |
| 13.45 | 2.91 | 4.6:1.0 | 50 | 0.94* |
| 11.38 | 3.75 | 3.0:1.0 | 50 | 0.87* |
| 8.87 | 5.81 | 1.5:1.0 | 50 | 0.83* |
| 5.69 | 9.00 | 1.0:1.6 | 50 | 0.82* |
| 3.34 | 11.63 | 1.0:3.5 | 50 | 0.83* |
| 2.84 | 12.29 | 1.0:4.3 | 50 | 0.84* |
| 1.42 | 14.59 | 1.0:10.3 | 50 | 0.88* |
| 0.71 | 15.60 | 1.0:21.5 | 50 | 0.88* |
| 0.36 | 15.85 | 1.0:44.6 | 50 | 0.89* |
| 0.18 | 15.28 | 1.0:85.9 | 50 | 0.85* |
| 0.09 | 15.60 | 1.0:175.6 | 50 | 0.86* |
| 0.04 | 15.82 | 1.0:356.1 | 50 | 0.87* |
| 0.00 | 18.21 | — | 50 | 1.00 |
| NH$_2$Cl & NHCl$_2$ @ pH 8.0 | | | | |
| 0.59 | 0.00 | — | 50 | 1.00 |
| 0.57 | 0.73 | 1.0:1.3 | 50 | 1.05 |
| 0.48 | 1.45 | 1.0:3.0 | 50 | 0.99* |
| 0.36 | 2.14 | 1.0:6.0 | 50 | 0.87* |
| 0.29 | 2.91 | 1.0:10.2 | 50 | 0.85* |
| 0.18 | 3.86 | 1.0:21.7 | 50 | 0.78* |
| 0.09 | 5.22 | 1.0:58.8 | 50 | 0.81* |
| 0.07 | 5.81 | 1.0:88.8 | 50 | 0.84* |
| 0.04 | 6.88 | 1.0:154.7 | 50 | 0.94* |
| 0.00 | 7.96 | — | 50 | 1.00 |

Table 1 shows a synergy between monochloramine and dichloramine. The synergy is affected by pH. For example, the synergistic ratio of monochloramine to dichloramine was much broader at pH 8 than pH 5. At the higher pH, monochloramine could be in a ratio of less than 1:1 or greater than 1:1 and still be synergistic. At pH 5, ratios greater than 1:1 (monochloramine to dichloramine) were synergistic. Lower pH provides greater synergy.

Example 2

In this example, a measured amount of monochloramine and a measured amount of dichloramine were added to a consortium of bacteria prepared to a density of approximately $1 \times 10^6$ cells per milliliter and the cell suspension incubated for a selected time. The consortium of bacteria is described above. The effectiveness of the combination of biocides was determined by measuring the number of bacteria that survived after the contact time. The efficacy of monochloramine, dichloramine, and combinations of the two actives were compared at different pH values. Bacterial consortia were prepared in mineral salts solutions with pH adjusted to selected values and challenged with monochloramine and dichloramine and combinations thereof. Samples for enumerating the number of surviving bacteria were collected at selected time intervals.

TABLE 2

Numbers of bacteria surviving after a 20 minute contact time with monochloramine (MCA), dichloramine (DCA) and combinations thereof. Numbers are log$_{10}$ transformations and represent the average of three values

| pH | 0.5 mg/l MCA | 1.0 mg/l MCA | 0.5 mg/l DCA | 1.0 mg/l DCA | 0.5 mg/l MCA + 0.5 mg/l DCA |
|---|---|---|---|---|---|
| 5.0 | 4.97 | 3.94 | 5.58 | 4.47 | 0.00 |
| 6.0 | 5.14 | 5.14 | 5.17 | 3.62 | 3.06 |
| 7.0 | 5.47 | 5.17 | 5.52 | 5.40 | 3.95 |
| 8.0 | 5.74 | 5.71 | 5.62 | 5.26 | 4.49 |

As is evident in table 2, a combination of monochloramine and dichloramine at a ratio of 1:1 was more effective at killing bacteria in the species defined consortium than either active alone. The table also indicates the effect of pH on the efficacy of monochloramine and dichloramine and the synergistic effect. The pH effect on synergy between monochloramine to dichloramine is evident by comparing efficacy (as indicated by the number of surviving bacteria after a 20-minute contact time) as a function of pH. That synergy was obvious at pH from 5 to 8 is illustrative of the potential utility of using the two actives together.

Example 3

Although synergy was detected when monochloramine and dichloramine were combined in a 1:1 ratio, the results of Example 1 illustrated that optimum ratios were larger than 1:1 (monochloramine to dichloramine). In this example, bacterial consortia were prepared with the pH of the mineral salts solution adjusted to selected levels immediately before the cells were added. Monochloramine was prepared to a desired concentration by mixing appropriate quantities of 30% ammonium hydroxide and 6.2% percent sodium hypochlorite in a volume of deionized water in such a manner as to achieve equimolar ratios of Cl$^-$ and NH$_2^+$. After preparation of the monochloramine solution, the purity of the solution was verified by determining its absorbance spectrum. To prepare a dichloramine solution, the pH of a monochloramine solution was adjusted to down to 3.0. This ensured conversion of the monochloramine to dichloramine. The spectral characteristics of the dichloramine solutions demonstrated that decreasing the pH of a monochloramine solution in deionized water did result in the formation of dichloramine. The concentrations of monochloramine and dichloramine in the solutions were confirmed by measuring total chlorine concentration by Hach DPD chlorine test. Selected ratios of monochloramine and dichloramine were added and numbers of bacteria surviving after a 20-minute contact time were determined. In this study, the 0.5 mg/l monochloramine and 0.5 mg/l dichloramine were tested. In addition, the ratios of monochloramine to dichloramine were adjusted by varying the amount of each active added to the cell suspension while keeping the total amount of chloramine added at 0.5 mg/l. For example, by adding 0.4 mg/l monochloramine and 0.1 mg/l dichloramine, the total amount added was 0.5 mg/l (as Cl$_2$) but the ratio was changed to 4:1.

Figure 1:
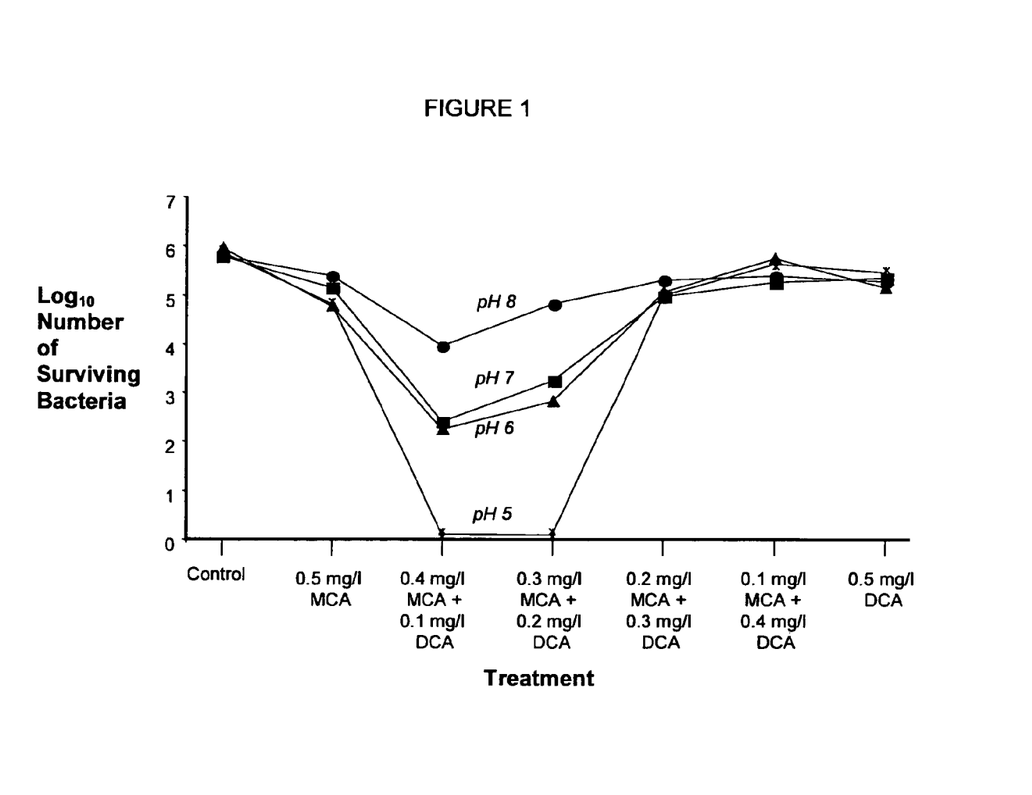
FIG. 1 Effect of pH on synergy between monochloramine and dichloramine.

FIG. 1 shows that the ratio of monochloramine to dichloramine affects the synergy. As the ratio of monochloramine to dichloramine decreases, the synergistic effect is enhanced. Lower pH increases the synergistic effect.

FIG. 1 shows the effect of pH on synergy between monochloramine and dichloramine. Bacteria were exposed to the designated concentrations for 20 minutes before the number of survivors was determined. MCA=monochloramine, DCA=dichloramine.

Example 4

Figure 2:
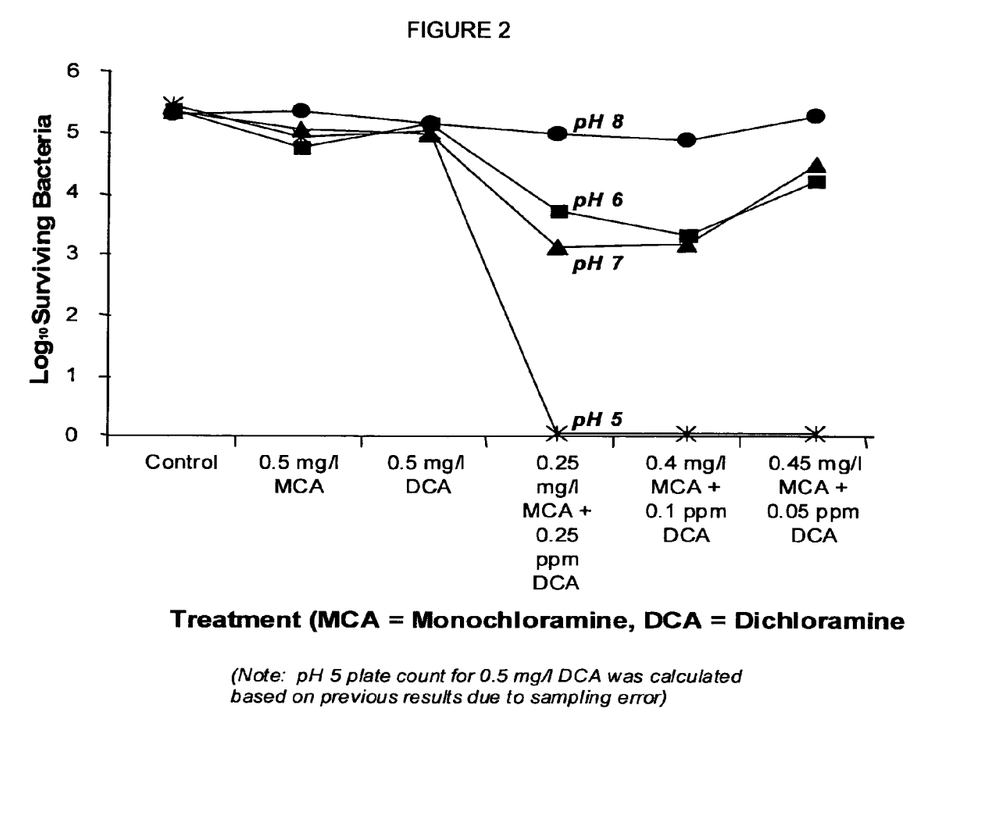
FIG. 2 Synergy of monochloramine and dichloramine.

In another dose challenge study using the dose protocol the range of desired ratios of monochloramine to dichloramine as well as the single actives was expanded from 1:1 to 10:1 (monochloramine to dichloramine). After a 20-min contact time, the numbers of surviving bacteria were determined. In this experiment, all systems were challenged with 0.5 mg/l (as $Cl_2$) active. As illustrated in FIG. 2, as the ratio of monochloramine to dichloramine increased from 1:1 to 10:1, so did the synergy, regardless of pH.

FIG. 2 shows the effect of pH and selected monochloramine to dichloramine ratios on bacterial consortia. Bacteria were exposed to the designated combinations of monochloramine and dichloramine for 20 minutes before numbers of survivors were determined The results presented in FIG. 2 are illustrative of the potential utility of using the two actives together to treat recirculating waters over a range of pH values.

Example 5

Monochloramine and bromamine were tested using the dose protocol and standard challenge assay. In this example, bromamine was prepared by reacting hypobromous acid (HOBr) with ammonium hydroxide to form monobromamine. Because monobromamine rapidly converts to dibromamine in solution at pH below 10, the bromamine used in the synergy assay consisted primarily of dibromamine. In this example, a range of ratios of monochloramine to bromamine was tested. The results demonstrated synergy with combinations of monochloramine to bromamine in the range of 15 parts monochloramine:1 part bromamine to 1 part monochloramine:50 parts bromamine. Ratios having more than 15 parts monochloramine to 1 part bromamine are expected to show synergy.

Figure 3:
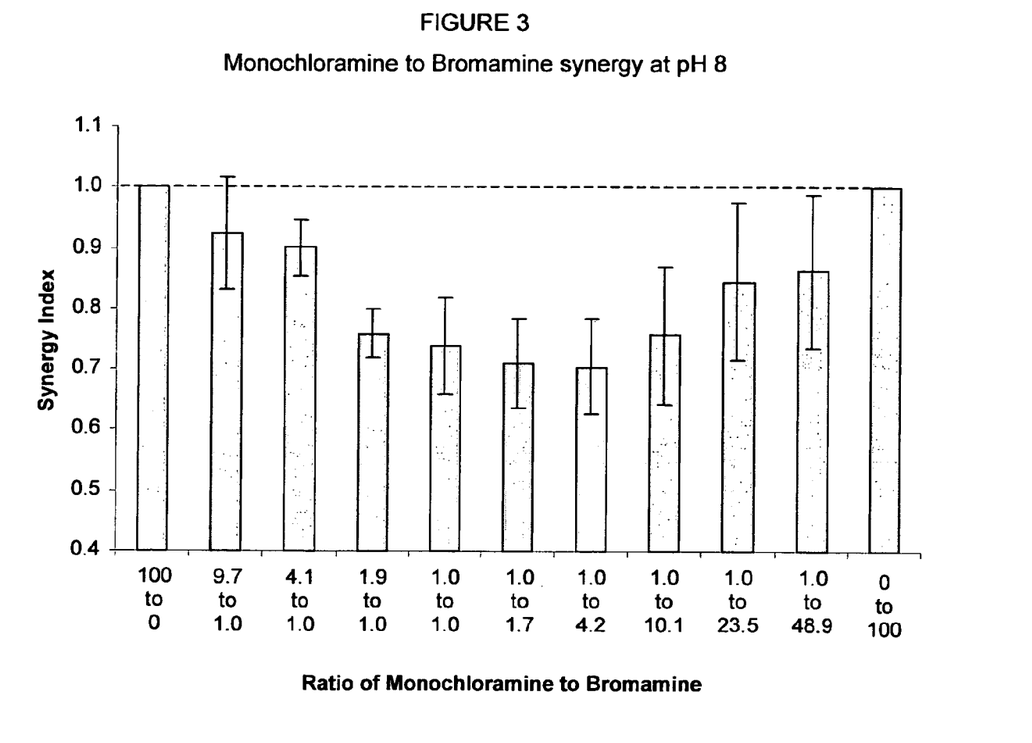
FIG. 3 Synergy of monochloramine and bromamine at pH 8.

FIG. 3 shows the results of synergy testing between monochloramine and bromamine at pH 8.0.

Figure 4:
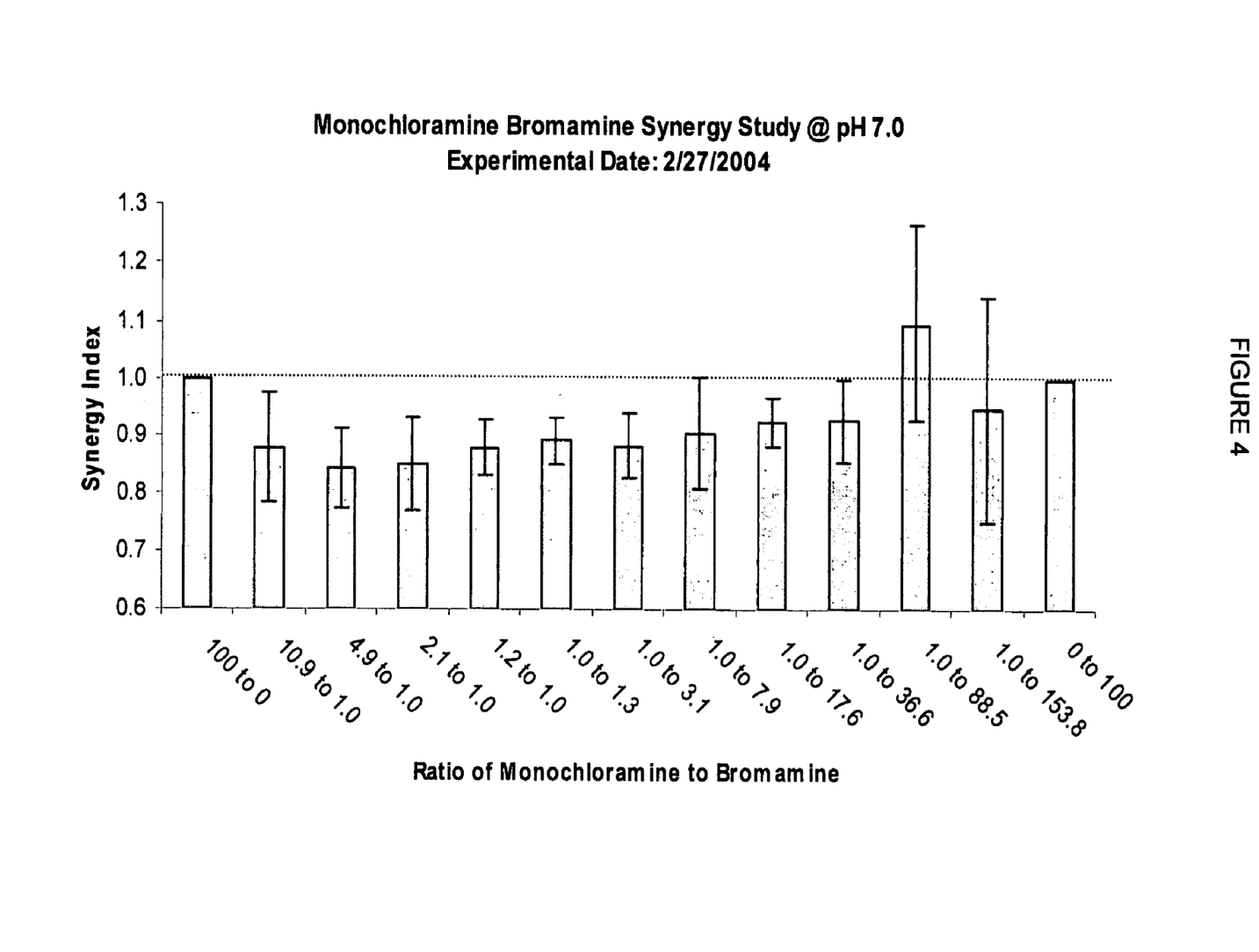
FIG. 4 Synergy of monochloramine and bromamine at pH 7.

FIG. 4 shows the results of synergy testing between monochloramine and bromamine at pH 7.0.

Figure 5:
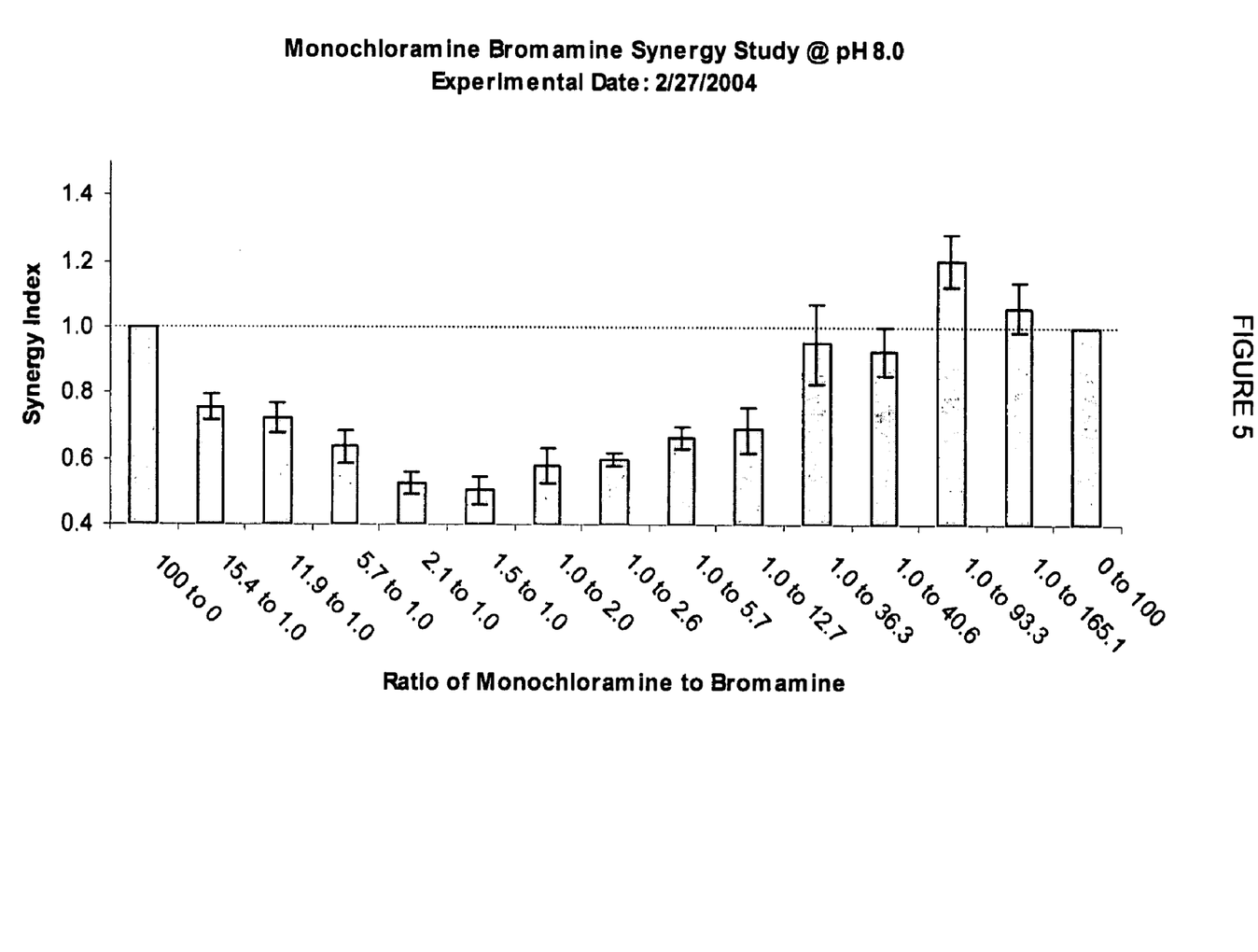
FIG. 5 Synergy of monochloramine and bromamine at pH 8.

FIG. 5 shows the results of synergy testing between monochloramine and bromamine at pH 8.0.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

What is claimed is:

1. A method for controlling the growth of bacteria in an aqueous system, comprises forming a blend of monochloramine and dichloramine with a ratio of monochloramine to dichloramine of from 1:1 to 9:1 and subsequently adding an effective amount of said blend to the aqueous system, wherein said aqueous system is a pulp and paper mill water system and has a pH in the range of from 5 to 7.

2. The method of claim 1, wherein the monochloramine is produced by contacting an ammonium or an amine source with a chlorinated oxidant or in the alternative by contacting the ammonium or the amine source with an oxidizer in the presence of a chlorine source.

3. The method of claim 2, wherein the amine source is selected from the group consisting of polyamines, primary amines, secondary amines, cyclic amines, aliphatic amines, aromatic amines, primary and secondary nitrogen containing polymers and combinations thereof.

4. The method of claim 2, wherein the ammonium source or the amine source is selected from the group consisting of dimethylamine, ethanolamine, ethylenediamine, diethanolamine, triethanolamine, dodecylethanolamine, hexdecylethanolamine, oleic acid ethanolamine, triethylenetetramine, dibutylamine, tributylamine, glutamine, dilaurylamine, distearylamine, tallow-methylamine, coca-methylamine, n-alkylamines, n-acetylglucosamine, diphenylamine, ethanol/methylamine, diisopropanolamine, n-methylaniline, n-hexyl-n-methylamine, n-heptyl-n-methylamine, n-octyl-n-methylamine, n-nonyl-n-methylamine, n-decyl-n-methylamine, n-dodecyl-n-methylamine, n-tridecyl-n-methylamine, n-tetra-decyl-n-methylamine, n-benzyl-n-methylamine, n-phenylethyl-n-methylamine, n-phenylpropyl-n-methylamine, n-alkyl-n-ethylamines, n-alkyl-n-hydroxyethylamines, n-alkyl-n-propylamines, n-propylheptyl-n-methylamine n-ethylhexyl-n-methylamine, n-ethylhexyl-n-butylamine, n-phenylethyl-n-methylamine, n-alkyl-n-hydroxypropylamines, n-alkyl-n-isopropylamines, n-alkyl-n-butylamines and n-alkyl-n-isobutylamines, n-alkyl-n-hydroxyalkylamines, hydrazine, urea, guanidines, biguanidines, and combinations thereof.

5. The method of claim 2, wherein the chlorinated oxidant is selected from the group consisting of chlorine, hypochlorite, hypochlorous acid, chlorinated isocyanurates, chlorinated hydantoins, and combinations thereof.

6. The method of claim 2, wherein the ammonium or the amine source is an ammonium salt or ammonia.

7. The method of claim 2, wherein the oxidant is selected from ozone, a peroxy compound or combinations thereof.

8. The method of claim 2, wherein the chlorinated oxidant comprises hypochlorous acid or hypochlorite.

9. The method of claim 1, wherein the dichloramine is produced by reacting an ammonium or an amine source with a chlorinated oxidant.

10. The method of claim 1, wherein the dichloramine is produced by decreasing the pH of a monochloramine-containing solution.

11. The method of claim 1, wherein the dichloramine is produced by changing the proportion of chlorine to nitrogen in a monochloramine-containing solution.

12. The method of claim 1, wherein the monochloramine is produced from an amine or ammonium source comprising ammonia or ammonium hydroxide.

13. The method of claim 1, wherein the monochloramine is produced from an amine or ammonium source comprising an ammonium salt.

14. The method of claim 13, wherein the ammonium salt is selected from the group consisting of ammonium sulfate, ammonium acetate, ammonium bicarbonate, ammonium carbonate, ammonium chloride, ammonium citrate, ammonium iodide, ammonium molybdate, ammonium nitrate, ammonium oxalate, ammonium persulfate, ammonium phosphate, ammonium sulfide, ammonium sulfamate and combinations thereof.

15. The method of claim 1, wherein the amount of monochloramine, on an active level basis, ranges from about 0.01 to about 1000 mg/l as $Cl_2$ based on the volume of the aqueous system being treated.

16. The method of claim 1, wherein the amount of monochloramine ranges from about 0.05 to about 200 mg/l as $Cl_2$ on an active level basis.

17. The method of claim 1, wherein the blend is continuously, intermittently, or alternately added to the aqueous system.

18. The method of claim 1, wherein the amount of dichloramine, on an active level basis, ranges from about 0.01 to about 1000 mg/l as $Cl_2$ based on the volume of the aqueous system being treated.

19. The method of claim 1, wherein the amount of dichloramine ranges from about 0.05 to about 200 mg/l as $Cl_2$ on an active level basis.

* * * * *